United States Patent [19]

Ali

[11] 4,247,453
[45] Jan. 27, 1981

[54] FOLIC ACID DERIVATIVES FOR USE IN RADIOIMMUNOASSAY

[75] Inventor: Akhtar Ali, Vernon Hills, Ill.

[73] Assignee: Abbott Laboratories, North Chicago, Ill.

[21] Appl. No.: 942,002

[22] Filed: Sep. 13, 1978

[51] Int. Cl.² ............................................ C07C 103/52
[52] U.S. Cl. ........................... 260/112.5 R; 23/230 B; 424/1; 252/301.1 R
[58] Field of Search ................ 260/112.5 R; 23/230 B

[56] References Cited
U.S. PATENT DOCUMENTS 3,989,812  11/1976  Barrett et al. ...................... 23/230 B

*Primary Examiner*—Paul M. Coughlan, Jr.
*Attorney, Agent, or Firm*—John J. McDonnell

[57] ABSTRACT

The present invention encompasses compounds I and II, mixtures of I and II and acid addition salts thereof wherein R is hydrogen or loweralkyl having 1-3 carbon atoms, as well as compounds wherein the phenol moiety is labeled with $^{125}I$ or $^{131}I$. The radiolabeled compounds are useful in radiochemical assaying for folic acid.

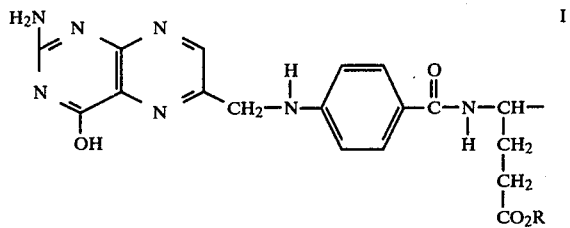

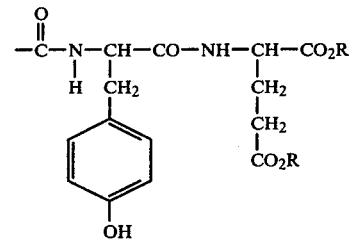

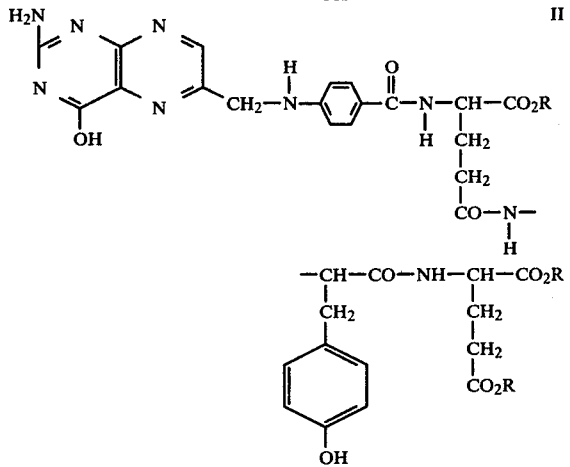

2 Claims, No Drawings

FOLIC ACID DERIVATIVES FOR USE IN RADIOIMMUNOASSAY

BACKGROUND OF THE INVENTION

The present invention relates to folic acid derivatives useful for radioassaying folic acid and its metabolites in biological fluids such as blood serum. There are many methods known for the radioassay of folic acid and its derivatives in biological fluid. Competitive binding of labeled folic acid (compounds of the present invention) and test sample folic acid for the folate binding protein(s) present in milk (Clinical Chem. 19, 1101, 1973) is a suitable method for determining folic acid.

U.S. Pat. No. 3,989,812 describes compounds of the formula

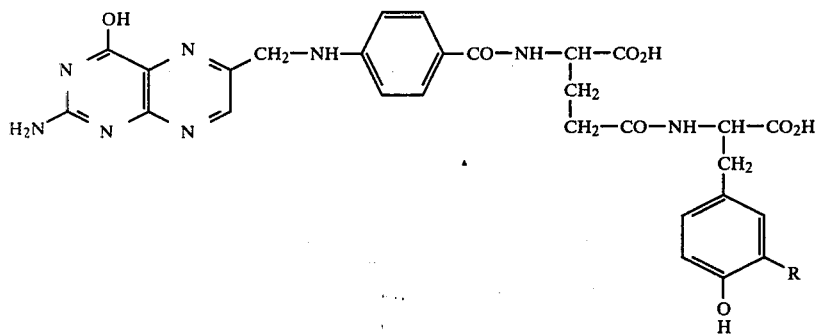

wherein R is $^{125}I$ or $^{131}I$ substituted in the phenol ring having utility for determining folic acid in serum.

Belgium Pat. No. 840,196 describes tyramine derivatives of folic acid labeled $^{125}I$ or $^{131}I$.

The compounds of the present invention are particularly distinct in that the labeled tyrosine moiety is not in the terminal position and that the terminal position is occupied by glutamic acid.

Labeled compounds of the present invention more closely resemble folic acid in that both have glutamic acid in the terminal position.

BRIEF DESCRIPTION OF THE INVENTION

The present invention encompasses compounds of the formula I and II

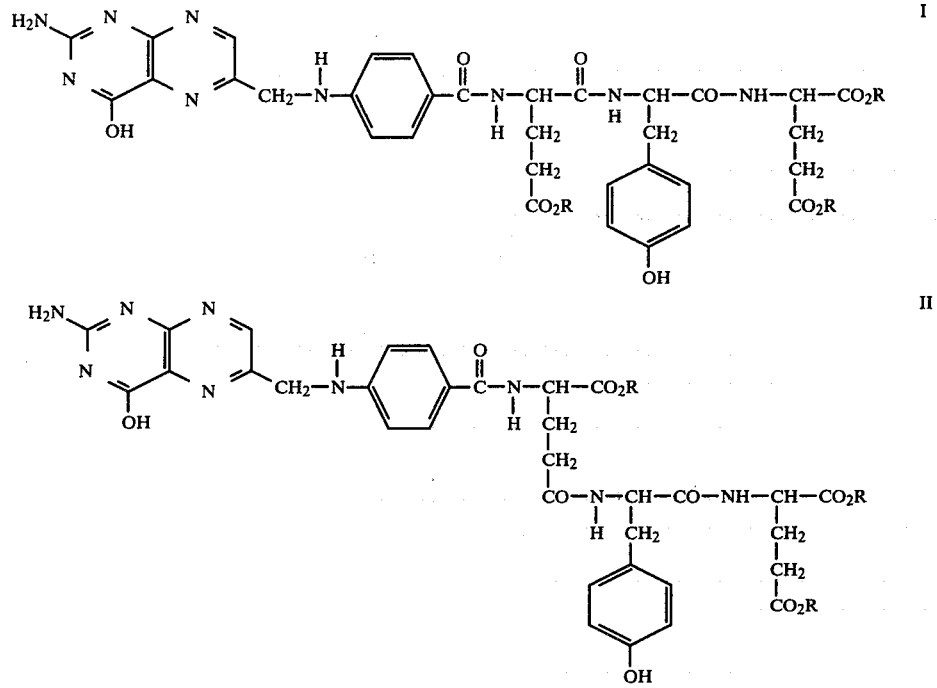

mixtures of I and II and acid addition salts thereof wherein R is hydrogen or loweralkyl having 1-3 carbon atoms.

The phenol moiety is labeled with $^{125}I$ or $^{131}I$ to provide radiolabeled folic acid derivatives useful for assaying for folic acid in biological fluids.

DETAILED DESCRIPTION OF THE INVENTION

Compounds of the present invention are prepared according to scheme A

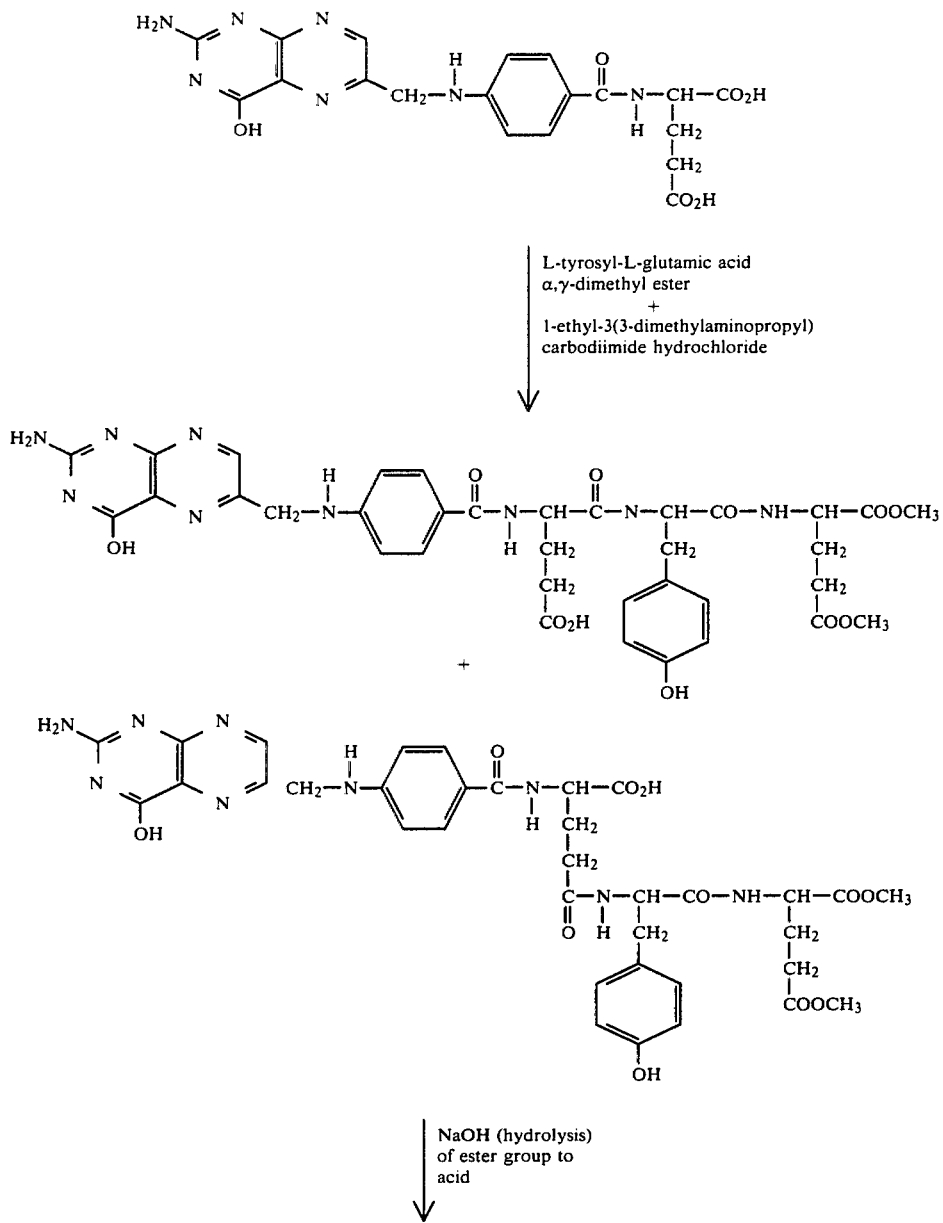

These compounds are separated by coventional chromatography techniques. The residual acid groups may be esterified by reaction with diazomethane or acid-catalyzed esterified with alcohols. Alternately, one of the carboxylic acid groups of the glutamic acid portion of the starting folic acid can be esterified providing a single condensation product. Esters are converted to acids by conventional base catalyzed hydrolysis.

Radioactive iodine, $^{125}I$ or $^{131}I$, is conveniently introduced into the phenol ring of tyrosine by the chloramine-T method of Greenwood et al., Biochem. J., 89, 114 (1963).

Compounds of the present invention are most conveniently used as the acid addition salt of organic and mineral acids such as hydrochloric, hydrobromic, hydroiodic, sulfuric, nitric, benzoic, acetic, trichloroacetic, toluenesulfonic acids and the like.

The following examples are intended to illustrate the present invention and not to limit the invention in spirit or scope.

EXAMPLE I

Folic Acid-Tyrosylglutamic Acid Reaction

Folic acid (485 mg, 1.1 mmole) is suspended in water (8.0 ml) and stirred magnetically, while a solution of L-tyrosyl-L-glutamic acid α,γ-dimethyl ester (39 mg, 1.17 mmole) in pyridine (8 ml) is added. To this reaction mixture is added 1-ethyl 3(3-dimethylaminopropyl)-carbodiimide hydrochloride (2.87 mg, 1.5 mmole). The mixture is stirred at 4° C. overnight. 20 ml of 0.5% sodium bicarbonate solution is added to the reaction mixture and filtered. The filtrate is acidified with 1 N hydrochloric acid to pH 3.0. The resulting precipitate is filtered and washed with about 20 ml of cold water.

This precipitate of the folic acid-tyrosylglutamic acid dimethyl ester is suspended by stirring in 10 ml of 0.2 N sodium hydroxide, while nitrogen gas is bubbled through the reaction mixture. After 15–20 minutes of stirring at room temperature, the clear solution is acidified with 1 N hydrochloric acid to pH 3.0. This precipitated material is filtered, washed with cold water and dried in a vacuum desiccator to provide a mixture of compound I and II where R is hydrogen. These compounds are separated by conventional techniques.

Iodination was performed by chloramine-T procedure, Biochem. J., 89, 114 (1963).

100 μl of 0.5 M sodium phosphate pH 7.5 is added to a glass test tube, followed by 10.0 mCi of NaI$^{125}$. To this solution is added 25 μl (8.3 μg) of folic acid-tyrosylglutamic acid in sodium bicarbonate solution and 50 μl of 0.4% chloramine-T solution in 0.05 M sodium phosphate buffer pH 7.5, respectively. After 60 seconds, mixing at room temperature, 50 μl of 0.8% sodium metabisulfite is added to the reaction mixture.

Incorporation of $^{125}$I into folic acid derivative is in excess of 85%. The purification of the iodinated reaction mixture is achieved by ion exchange followed by cellulose column chromatography

Binding Activity of Folate Derivatives

The $^{125}$I folate compounds are tested for their ability to bind to specific folate binders.

Partially purified bovine milk and goat's milk folate binders (J. Dairy Res., 36, 435 (1969)) are diluted serially with 0.05 M borate buffer containing 0.1% dithiothreitol and 0.05% gelatin pH 9.0. $^{125}$I folate (0.01–0.02 μCi) is added to 0.5 ml of each respective binder dilution (final reaction volume is 0.6 ml). The mixture is vortexed and allowed to incubate 45 minutes at room temperature. At the end of the incubation period, 1 ml of a 0.7% dextran-coated charcoal suspension is added to each tube, vortexed and allowed to stand 5 minutes at room temperature. The tubes are centrifuged at 1000 g for 15 minutes. The supernatants are decanted into clean tubes and counted in a gamma scintillation counter.

Results

The $^{125}$I folate derivatives typically show a maximum binding ability of between 75–90%.

Determination of Folate Concentration in Biological Fluids Preparation of Samples Serum is obtained, free of hemolysis and stored at 4° C. for 24 hours. For longer storage periods samples are stored at −20° C.

Samples for red cell folate determinations are prepared by diluting 1 part of whole blood with 19 parts of a 0.2% ascorbic acid solution. Samples are allowed to stand at room temperature for 1½ hours to allow for hydrolysis of folate polyglutamates. Samples are then stored at −20° C. if not used immediately.

Folate Assay

Pteroylglutamic acid (folic acid) is diluted serially with 0.05 M borate buffer containing 0.05% gelatin and 0.1% dithiothreitol; pH 9.0. The concentrations of folic acid used are 0, 2.5, 5, 10, 15 and 20 ng/ml.

Borate buffer (0.4 ml) is added to a series of polypropylene tubes. To this solution is added 0.05 ml of appropriate standard dilution or sample (serum or hemolysate).

The contents of the tubes are mixed and heated in a boiling water bath for 15 minutes. The tubes are loosely covered during the extraction.

The tubes are cooled to room temperature and 0.10 ml of $^{125}$I folate derivative in borate buffer (0.01–0.02 μCi) is added to each tube followed by 0.10 ml of an appropriate dilution of folate milk binder in borate buffer to give about 50% binding. The tubes are vortexed and allowed to stand at room temperature for 45 minutes. At the end of the incubation period, 1 ml of a cold 0.7% dextran-coated charcoal suspension is added to each tube, vortexed and allowed to stand 5 minutes at room temperature. The tubes are then centrifuged at 1000 xg for 15 minutes. The supernatants are decanted into clean tubes and counted in a suitable scintillation counter.

Results

The folate in the patient samples are determined by comparison with a logit-log plot of the standard curve. Red cell folates are corrected for dilution and hematocrit (Clin. Biochem., 6, 274 (1973)).

What is claimed is:

1. A compound of the formula I or II,

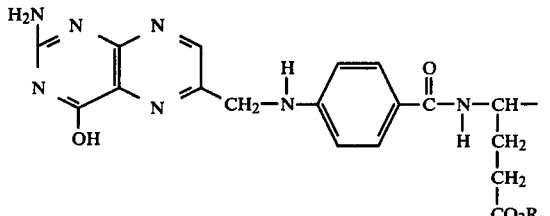

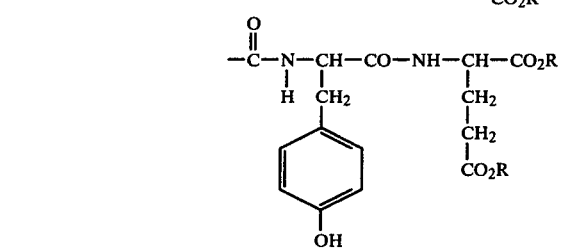

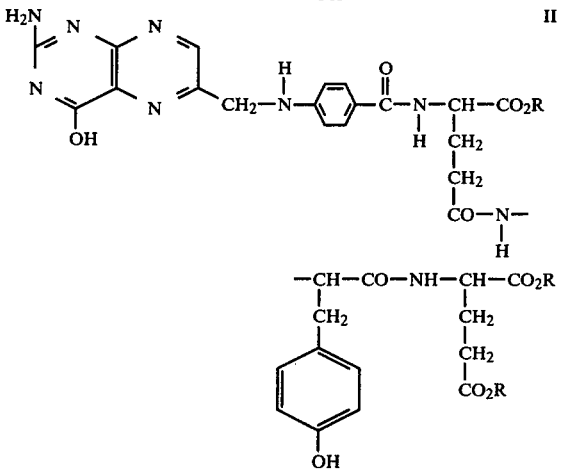

and acid addition salts thereof wherein R is hydrogen and wherein the phenol ring is labeled with $^{125}$I or $^{131}$I.

2. A mixture of compounds I and II

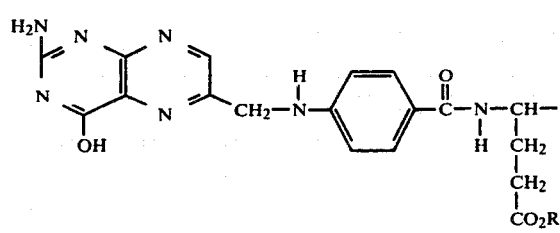
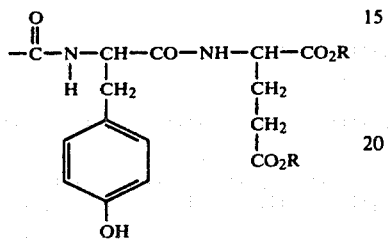
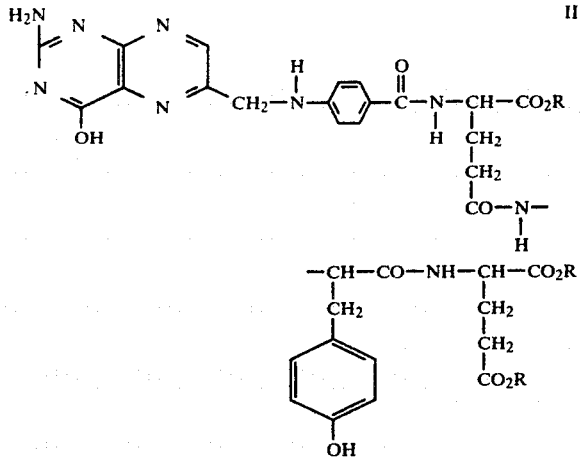
and acid addition salts thereof wherein R is hydrogen and wherein the phenol ring is labeled with $^{125}$I or [131]I.
* * * * *